United States Patent
Woo et al.

(10) Patent No.: US 6,611,963 B2
(45) Date of Patent: Sep. 2, 2003

(54) WIRE BAND EARMUFF

(75) Inventors: Edwin Woo, Chula Vista, CA (US); William Nyugen, San Diego, CA (US); Thomas W. Fleming, San Diego, CA (US)

(73) Assignee: Bacon USA Safety, Inc., San Diego, CA (US)

( * ) Notice: Subject to any disclaimer, the term of this patent is extended or adjusted under 35 U.S.C. 154(b) by 0 days.

(21) Appl. No.: 10/039,823

(22) Filed: Oct. 26, 2001

(65) Prior Publication Data

US 2003/0079275 A1 May 1, 2003

(51) Int. Cl.[7] .................................................. A42B 1/06
(52) U.S. Cl. ......................................................... 2/209
(58) Field of Search ..................... 2/209, 423; 181/129; 381/372, 374, 376, 379; 128/866, 867

(56) References Cited

U.S. PATENT DOCUMENTS

| 2,149,341 A | | 3/1939 | Harrison | |
|---|---|---|---|---|
| 2,801,423 A | * | 8/1957 | Shaw et al. ..................... | 2/209 |
| 2,858,544 A | | 11/1958 | Roth | |
| D203,677 S | | 2/1966 | Spilman et al. | |
| 3,505,684 A | | 4/1970 | Hutchinson et al. | |
| 3,562,816 A | | 2/1971 | Hutchinson | |
| 3,719,954 A | | 3/1973 | Beguin | |
| 3,862,451 A | * | 1/1975 | Miller et al. .................... | 2/209 |
| 4,209,264 A | | 6/1980 | Hellberg | |
| 4,471,496 A | | 9/1984 | Gardner, Jr. et al. | |
| 4,541,302 A | * | 9/1985 | Yamamoto et al. ......... | 74/502.4 |
| 4,756,028 A | * | 7/1988 | Scanlon ......................... | 2/209 |
| 5,278,999 A | * | 1/1994 | Brown et al. .................. | 2/209 |
| 5,406,037 A | | 4/1995 | Nageno et al. | |
| 5,528,774 A | * | 6/1996 | Sanders ......................... | 2/209 |
| 6,449,806 B1 | * | 9/2002 | Engelhard et al. ............. | 24/3.1 |

FOREIGN PATENT DOCUMENTS

WO    WO 94/09734    5/1994

* cited by examiner

*Primary Examiner*—Rodney M. Lindsey
(74) *Attorney, Agent, or Firm*—Leon D. Rosen

(57) ABSTRACT

A banded earmuff for protecting a worker's hearing, includes a band (12) formed of a wire frame (34) and a flexible polymer sheath (32) around much of the wire frame and a pair of pods (14,16) that press around the wearer's ears. The wire frame includes parallel wire lengths (50, 52) with opposite end parts joined by loops (70, 72). Each pod that seals around the ear has a mount (40) that is coupled to the wire length end parts. Each mount has a groove (42) with opposite sides that receive the pair of wire length end parts. This allows the pod to pivot on the wire length end parts, and to also slide along them. The sheath is molded with a pair of slits (114, 116), and middle length parts of the wire frame are installed through the slits into passages (54, 56) in the sheath.

13 Claims, 3 Drawing Sheets

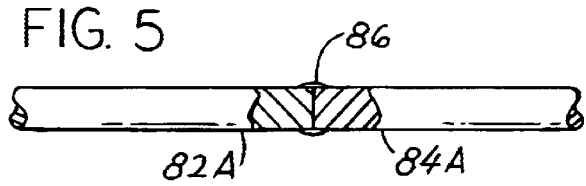
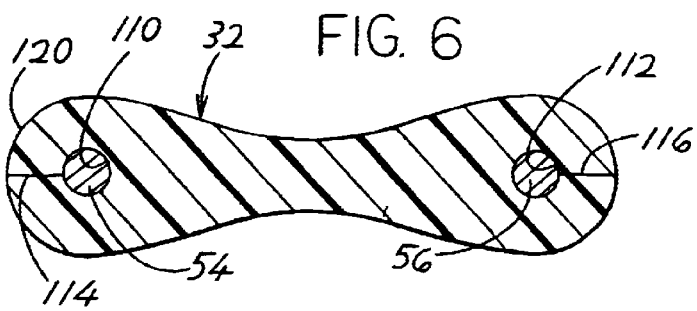
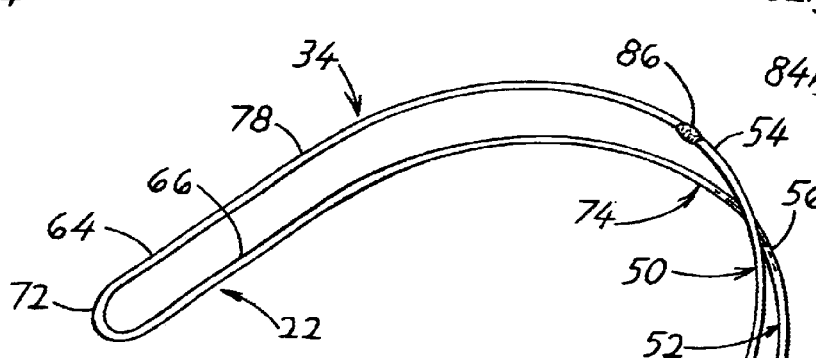
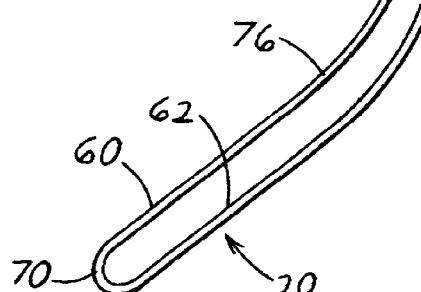
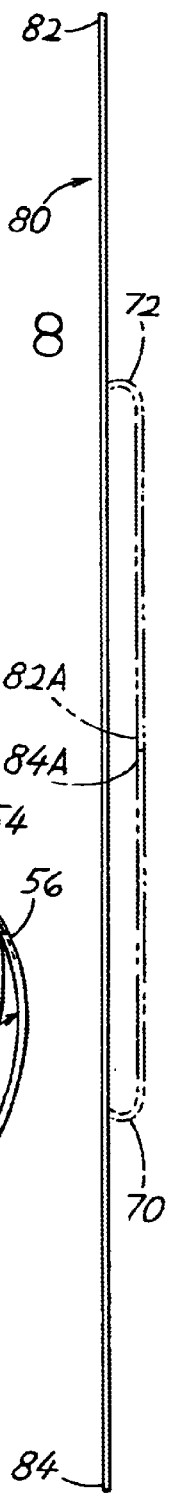

WIRE BAND EARMUFF

BACKGROUND OF THE INVENTION

A person's hearing can be protected by a banded earmuff which includes a pair of pods with openings that receive much of each ear and a band that connects the pods and that presses them together and against the sides of the person's head. The band can extend behind the person's head, but some people find it more comfortable to have the band extend around the top of the head or under the chin. It is desirable to allow the band to pivot with respect to the pods and to enable adjustment of effective band length so the band can fit closely against the person's head in any orientation and for persons with different size heads.

Previously, banded earmuffs that allow adjustment of band length and pivoting of the band with respect to the ear pods, were complex and expensive. This often resulted in employers not providing banded earmuffs, but only earplugs that had to be inserted into the person's ear canal. Some people found such earplugs to be uncomfortable and/or difficult to properly install. A versatile banded earmuff of simple and low cost construction, would enable banded earmuffs to be more widely used.

SUMMARY OF THE INVENTION

In accordance with one embodiment of the present invention, a banded earmuff is provided which is of simple and low cost construction, and yet which is versatile to allow the band to pivot to different orientations and change its effective length while keeping the pods securely pressed against the head area around each ear. The band includes a wire frame with parallel wire lengths that extend around the head and that have pairs of wire length end parts that are joined in loops and that are connected to the ear pods. Each pod has a mount with a 360° groove, and each pair of wire length end parts lie in opposite sides of the groove. The pair of wire length end parts can move around the groove to change the orientation of the band, and can slide along the groove to change the effective length of the band. This allows the band to have a fixed length between the loops at its opposite ends, and function as though it were a band of variable length.

The band includes a sheath of flexible polymer material covering the middle portions of the wire lengths. The sheath has a pair of passages that each receives the middle part of each wire length. The sheath can be extruded with a pair of slits each leading from one of the passages to the outside of the sheath, and the wire length middle parts can be inserted through the slits into the passages. The wire frame is formed of a single original piece of wire that is bent, with opposite ends of the original wire butt welded together. The butt weld lies in one of the sheath passages.

The novel features of the invention are set forth with particularity in the appended claims. The invention will be best understood from the following description when read in conjunction with the accompanying drawings.

BRIEF DESCRIPTION OF THE DRAWINGS

FIG. 5 is a partially sectional view showing ends of an original wire which have been butt welded together.

FIG. 6 is a sectional view taken on line 6—6 of FIG. 3.

FIG. 7 is an isometric view showing only the wire frame of the band of the earmuff of FIG. 3.

FIG. 8 is a front elevation view of an original wire which is bent and welded to form the wire frame of FIG. 7, and showing, in phantom lines, the original wire bent to its final orientation.

DESCRIPTION OF THE PREFERRED EMBODIMENTS

Figures 1, 2:
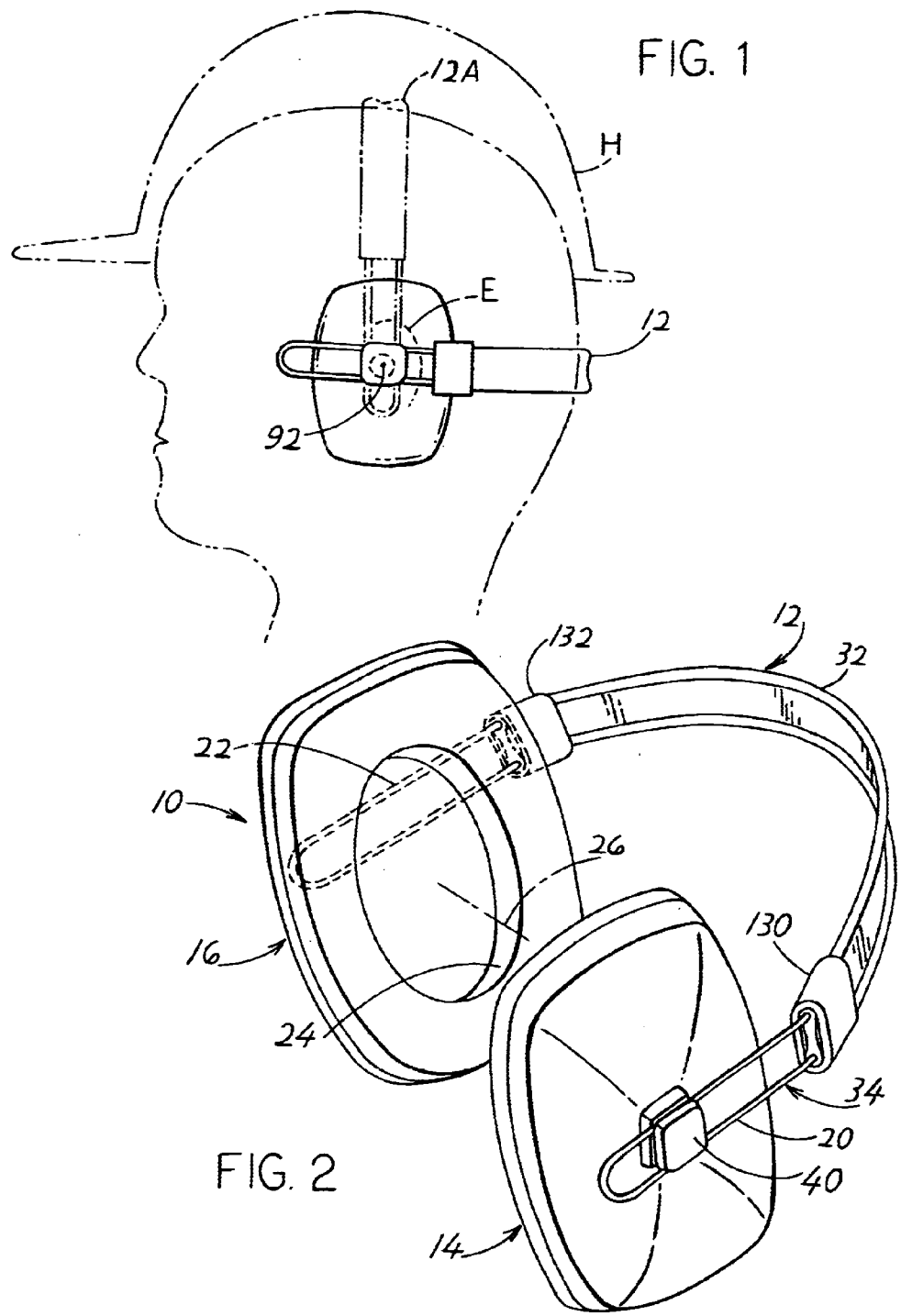
FIG. 1 is a side elevation view of a banded earmuff of the present invention with the band worn behind a person's head, the figure also showing, in phantom lines, the band worn above the head and showing the person and a helmet in phantom lines.
FIG. 2 is an isometric view of the banded earmuff of FIG. 1.

FIG. 2 illustrates a banded earmuff 10 which includes a band 12 for extending halfway around the wearer's head, and a pair of pods 14, 16 at opposite end portions 20, 22 of the band. The band is resilient and not only holds the pods but presses them against opposite sides of the wearer's head. Each pod has an elongated ear-receiving opening 24, and as indicated in FIG. 1, most of each ear E is received in one of the openings. FIG. 2 shows that the ear-receiving opening 24 has an axis 26 which is the axis of the pod. The banded earmuff can be worn in the most common position shown in solid lines in FIG. 1 wherein the band lies behind a person's head, especially when the person wears a helmet J. It is also possible to wear the banded earmuff in the position 12A above the top of the head, or even under the chin.

Figure 3:
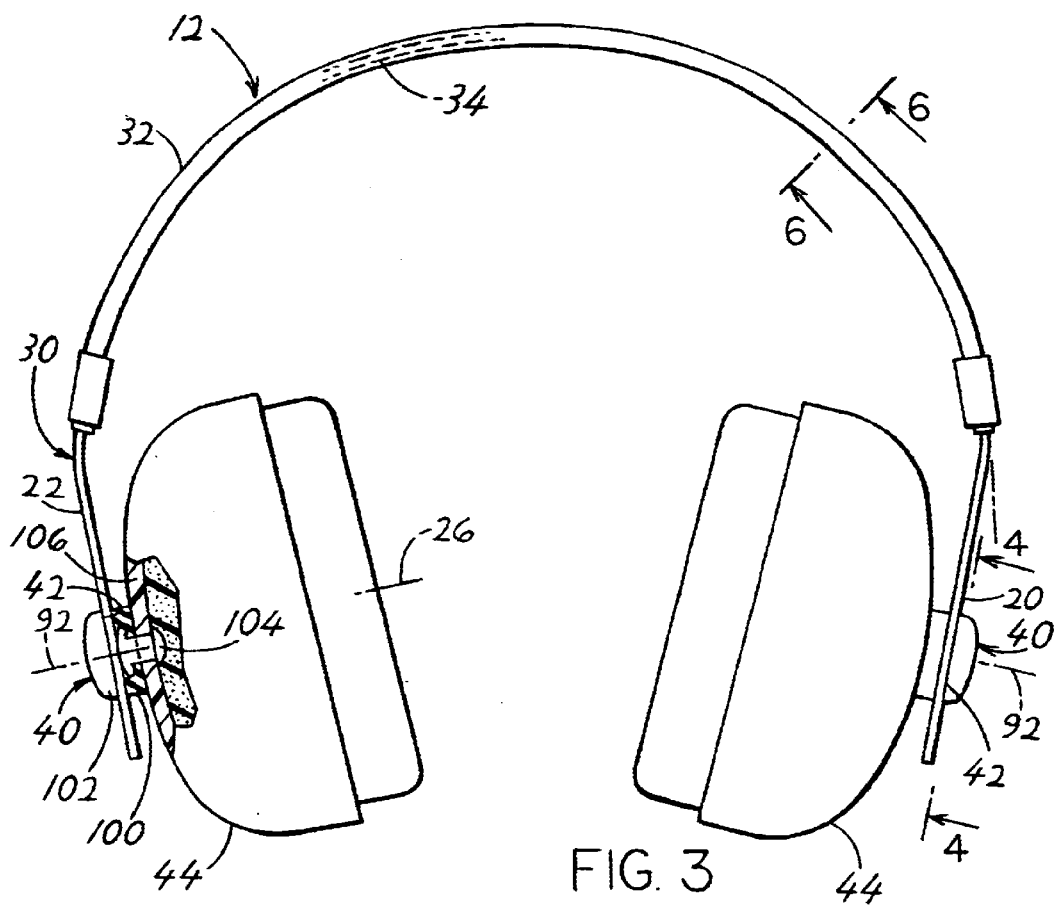
FIG. 3 is a front elevation view of the banded earmuff of FIG. 2.

FIG. 3 shows that the band 12 includes a wire frame 30 and a flexible polymer sheath 32 lying around a middle portion 34 of the band. Each pod has a mount 40 with a groove 42, and each wire end portion 20, 22 has parallel wire length end parts that lie in the groove. Each mount lies on an outer side 44 of a pod, opposite the ear-receiving opening of the pod.

FIG. 7 shows the wire frame 34 alone, showing that it has two parallel wire lengths 50, 52 with curved wire length middle parts 54, 56 and straight wire length end parts 60, 62, 64 and 66. Each pair of parallel wire lengths end parts such as 60, 62 form a corresponding band end portion 20 or 22. Each pair of wire length end parts is joined by a wire connecting part in the form of a loop 70, 72. The wire length middle parts 54, 56 form a wire frame middle portion 74. A pair of bends at 76, 78 of about 20° each, results in proper orientation of the band end portions.

The wire frame is preferably formed from a single length of original wire shown at 80 in FIG. 8. The original wire is bent to form the loops 70, 72 at opposite ends of the wire frame. The ends of the original wire lie close together at 82A, 84A where they are joined together. Joining is preferably by welding (which includes brazing), although a thin sleeve can be used which receives the wire ends and is crimped or otherwise joined to them. FIG. 7 shows the joint 86 of the original wire ends, while FIG. 5 is an enlarged view that shows a butt weld joint 86 at the wire ends 82A, 84A.

Figure 4:
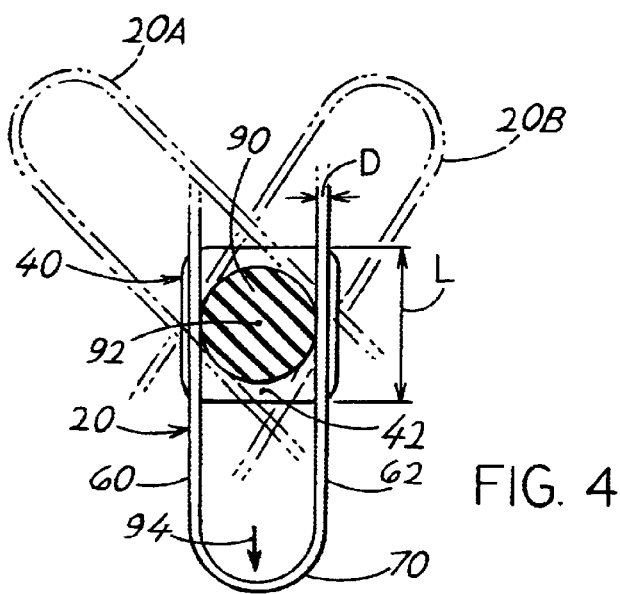
FIG. 4 is a sectional view taken on line 4—4 of FIG. 3, and showing different orientations of the wire band end portion.

FIG. 4 shows a pair of wire length end parts 60, 62 lying in opposite sides of a groove 42 in the mount 40. In the absence of the post part 90 of the mount, the end length parts 60, 62 would move closer together, so they press firmly against opposite sides of the post part 90. The wire length end parts 60, 62 of the band end portion 20, can rotate to any orientation around the groove axis 92. Two additional orientations 20A and 20B are shown. In addition, the band end portion 20 can slide perpendicular to the axis 92. Thus, if the band end portion 20 is in the orientation 20 and it is found that the band effective length should be shortened, the band end portion at 20 is slid in the direction 94 to effectively shorten the band, that is, to reduce the length around the head between the opposite pods.

The post part 90 of each mount, and the inner and outer parts 100, 102 (FIG. 3) of each mount are preferably formed of elastomeric material. This allows the wire end portion such as 22 to pivot by a plurality of degrees about axes that are perpendicular to the groove axis 92, to allow each pod to assume an orientation wherein it presses substantially uniformly against the side of the head of the person. It is only necessary for one of the parts 100, 102 to be formed of elastomeric material, although applicant constructs both parts to provide greater flexibility. The mount can be formed with a rigid stud 104 with an enlargement lying in an elastomeric outer portion beyond the outer side 44 of the pod, and another head lying against the inside of the shell 106 of the pod.

FIG. 4 shows that each wire length end part such as 62 is captured in the groove along a considerable length L, which is a plurality of times the diameter D of the wire, and preferably at least three times the wire diameter. The minimum length of capture is about 70% L. This controls the relative orientation of the mount end wire. However, since the portion of the mount engaging the wire is of elastomeric material, there can be several degrees of pivoting of the pod relative to the mount about axes perpendicular to the mount axis 92. The radial depth of the groove is greater than the diameter D of the wire. Although the post part is shown to be of round cross-section, it could have flat spots.

FIG. 6 is a sectional view of the sheath 32 of the band. The sheath is formed of a flexible polymer material, and has a pair of parallel sheath passages 110, 112 extending along its length, that each receives one of the wire length middle parts 54, 56. Applicant forms the sheath by extrusion. The extrusion molded sheath is formed with a pair of slits 114, 166 that each extends from one of the passages to the outside surface or outside 120 of the sheath. The slits are opened to allow the wire length middle parts to pass through the slits into the passages. The slits then can be left unsealed or can be sealed together by heat. The polymer sheath provides a "soft" feel to the band, especially the portion that lies against the head of the wearer. It is noted that the joint 86 where the original wire ends are welded together, lies in the sheath. Applicant prefers to place a stretch rubber band 130, 132 around each end of the sheath to prevent the slits from opening, although they resist opening anyway.

In a banded earmuff that application has constructed, the wire has a diameter D of 2 mm and the wire lengths are separated by 13.50 mm. The band is usually worn behind the head as shown at 12 in FIG. 1. However, the band is sometime worn higher or lower, which requires pivoting about the axis 92. The ability to vary the effective length of the band enables changes to accommodate variations in the size of the person's head and exact orientation of the band on that person's head. The elastomeric mount and narrow band ends, allow the pods to press firmly against the head areas around the person's ears.

Thus, the invention provides a banded earmuff which enables pivoting of the band to different orientation around the wearer's head, which enables changing of the effective length of the band, and which enables several degrees of pivoting about an axis perpendicular to the mount axis. This is accomplished with an earmuff having a band of simple and low cost construction to enable the earmuff to be sold at a low price. Each ear pod has a mount with a groove that extends around most and preferably the entire axis of the mount, with each band end portion comprising a pair of substantially parallel wire length end parts lying in opposite sides of the groove. The pair of wire length end parts can turn, or pivot around the groove to hold the band at any orientation within a wide angle of over ¾th of a full circle, such 360°. The mount also allows the band end portions to slide so as to change the effective length of the band. The walls of the mount groove are preferably of elastomeric material to allow the pod to change orientation by a plurality of degrees about axes perpendicular to the mount axis. The band includes a wire frame formed from a single original wire which is bent and which has ends joined together as by welding. A sheath of flexible polymer material encloses a middle portion of the wire frame. The sheath is molded as by extrusion, and has a pair of slits that facilitate insulation of wire frame middle length parts into passages of the sheath.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A banded earmuff which includes a band for extending about halfway around the wearer's head and a pair of pods at opposite end portions of the band for each pressing against a head area around an ear of the wearer, wherein said band includes a wire frame, and each of said band end portions includes a pair of spaced and largely parallel wire length end parts of a wire having a predetermined diameter and a connecting part that joins ends of said wire length end parts, and wherein each of said pods has an outer side facing away from the person's head and has a mount projecting from said pod outer side, each mount having a groove with a groove axis, said pairs of wire length end parts each being pivotable about the corresponding one of said groove axes to enable the band end portions to extend in different directions relative to the corresponding pod, wherein:

each of said grooves has a radial depth that is greater than the diameter of said wire, and the length of wire on each side of said groove which lies completely in said groove is at least three times the diameter of said wire, to thereby resist tilt of each pod about axes perpendicular to the axis of the pod.

2. A banded earmuff which includes a band for extending about halfway around the wearer's head and a pair of pods at opposite end portions of the band for each pressing against a head area around an ear of the wearer, wherein said band includes a wire frame, and each of said band end portions includes a pair of spaced and largely parallel wire length end parts and a wire connecting part that joins ends of said wire length end parts, and wherein each of said pods has an outer side facing away from the person's head and has a mount projecting from said pod outer side, each mount having a groove with a groove axis, said pairs of wire length end parts each being pivotable about the corresponding one of said groove axes to enable the band end portions to extend in different directions relative to the corresponding pod; wherein:

said frame extends along the length of said band and includes two substantially parallel wire lengths that form said wire length end parts, and that form parallel wire length middle parts that connect said wire length end parts;

said wire frame comprising an original wire that is bent to form said wire connecting parts, said original wire having opposite ends lying along one of said wire length middle parts where said opposite ends are joined together.

3. A banded earmuff which includes a band for extending halfway around the wearer's head and a pair of pods at opposite end portions of the band for each pressing against a head area around an ear of the wearer, wherein:

said band includes a wire frame that includes a pair of spaced and parallel wire lengths forming pairs of wire length middle parts and two pairs of wire length end parts, each pair of wire length end parts coupled to a different one of said pods;

said band includes a sheath of flexible polymer material having a pair of elongated passages, with each wire length middle part lying in one of said passages;

said sheath having at least one slit that extends from each of said sheath passages to the outside of said sheath, to thereby allow installation of said wire length middle parts in said sheath passages;

an elastomeric band extending around opposite ends of said sheath.

4. A banded earmuff which includes a band for extending halfway around the wearer's head and a pair of pods at opposite end portions of the band for each pressing against a head area around an ear of the wearer, wherein said band includes a wire frame that includes a pair of spaced and parallel wire lengths forming pairs of wire length middle parts and two pairs of wire length end parts, each pair of wire length end parts coupled to a different one of said pods, said band includes a sheath of flexible polymer material having a pair of elongated passages, with each wire length middle part lying in one of said passages, said sheath having at least one slit that extends from each of said sheath passages to the outside of said sheath, to thereby allow installation of said wire length middle parts in said sheath passages, wherein:

said wire frame comprises a single original wire that is bent to form said pair of wire length middle parts that connect each pair of wire length end parts, with said original wire having ends that are joined in series in an end joint, with said end joint lying in one of said sheath passages.

5. The banded earmuff described in claim 4 wherein:

said original wire ends abut one another and are welded together.

6. A banded earmuff which includes a band for extending about halfway around the wearer's head and a pair of pods at opposite end portions of the band for each pressing against a head area around an ear of the wearer, wherein each of said band end portions includes a pair of spaced and largely parallel wire length end parts and a wire connecting part that joins ends of said wire length end parts, and wherein each of said pods has an outer side facing away from the person's head, and has a mount projecting from said pod outer side, each mount having a groove with a groove axis, said pairs of wire length end parts each being pivotable about the corresponding one of said groove axes to enable the band end portions to extend in different directions relative to the corresponding pod, wherein:

each of said mounts is formed of elastomeric material, to allow said pods to pivot a plurality of degrees about axes that are perpendicular to the groove axes.

7. A low cost band earmuff that includes a band that is constructed to fit about halfway around a wearer's head and that has opposite band end portions, said band earmuff including a pair of ear pods each mounted on one of said band end portions, wherein:

said band includes a wire frame that is bent to extend about halfway around a person's head and that has opposite wire frame end portions for lying at opposite sides of the person's head and forming at least part of said opposite band end portions, said wire frame including two substantially parallel wire lengths that are bent into a connecting part at each of wire frame end portions, said parallel wire lengths each having a wire length middle part lying between said wire frame end portions;

said pods are each mounted on one of said wire frame end portions;

said wire frame comprising an original wire that is bent to form said connecting parts, said original wire having opposite ends lying along one of said parallel wire length middle parts, said opposite ends being joined together.

8. The earmuff described in claim 7 including:

a sheath of polymer material enclosing said wire length middle parts, said sheath having a pair of parallel sheath passages that each receives one of said wire length middle parts, including said joined opposite ends of said original wire;

said sheath having at least one slit that extends from each of said sheath passages to the outside of said sheath, to thereby allow installation of said wire length middle parts in said sheath passages.

9. The earmuff described in claim 7 including:

a sheath of flexible polymer material, said sheath having a pair of passages that each receives one of said wire length middle parts;

said sheath having a pair of slits that extend along the length of each passage and that connects the passage to an outside of the sheath, to thereby enable easy installation of the wire support length middle portions in the sheath passages.

10. A banded earmuff which includes a band for extending halfway around the wearer's head and a pair of pods at opposite end portions of the band for each pressing against a head area around an ear of the wearer to block noise, wherein:

each of said band end portions includes a wire with an end portion bent into a loop and with a pair of parallel opposite wire length end parts;

each of said pods has an inner side that faces the ear and an outer side, and each pod has a mount on its outer side, each mount forming a pair of opposite groove parts, and each pair of parallel wire length end parts lies in one of said groove parts;

each of said pair of parallel opposite wire length end parts being slidable along its length in the corresponding groove part so as to change the effective length of said band, and each of said pair of parallel wire length end parts being straight to avoid tilting the corresponding pod when the pair of wires are sliding along one of said pair of groove parts.

11. The earmuff described in claim 10 wherein:

said band is of fixed length between said loops, so adjustment of band length is solely by sliding of at least one pair of parallel wire length end parts along the pair of groove parts in the corresponding pod.

12. The earmuff described in claim 10 wherein:

each of said groove parts has a radial depth that is greater than the diameter of said wire, and the length of wire in each side of said groove parts which lies completely in the groove part is at least three times the diameter of said wire, to thereby resist tilt of each pod.

13. A banded earmuff which includes a band for extending halfway around the wearers head and a pair of pods at opposite end portions of the band for each pressing against a head area around an ear of the wearer, wherein:

said band includes a wire frame that includes a pair of spaced and parallel wire lengths forming pairs of wire length middle parts and two pairs of wire length end parts, each pair of wire length end parts coupled to a different one of said pods;

said band includes a sheath of flexible polymer material having a pair of elongated passages, with each wire length middle part lying in one of said passages; said sheath has rounded opposite sides and smooth top and bottom surface that connect the rounded opposite sides;

said sheath having a pair of slits that each extends from each of said sheath passages to the outside of said sheath, to allow installation of said wire length middle parts in said sheath passages;

each of said slits has opposite slit sides that touch one another.

* * * * *